(12) United States Patent
Butters et al.

(10) Patent No.: US 10,238,426 B2
(45) Date of Patent: Mar. 26, 2019

(54) BLADE FIXATION FOR ANKLE FUSION AND ARTHROPLASTY

(71) Applicant: ENGAGE MEDICAL HOLDINGS, LLC, Los Angeles, CA (US)

(72) Inventors: Joshua A. Butters, Chandler, AZ (US); Jeffery D. Arnett, Gilbert, AZ (US); Hyun Bae, Santa Monica, CA (US)

(73) Assignee: Engage Medical Holdings, LLC, Los Angeles, CA (US)

( * ) Notice: Subject to any disclaimer, the term of this patent is extended or adjusted under 35 U.S.C. 154(b) by 0 days.

(21) Appl. No.: 15/339,415

(22) Filed: Oct. 31, 2016

(65) Prior Publication Data

US 2017/0042576 A1   Feb. 16, 2017

Related U.S. Application Data

(63) Continuation of application No. 13/747,791, filed on Jan. 23, 2013, now Pat. No. 9,480,511.

(60) Provisional application No. 61/589,721, filed on Jan. 23, 2012.

(51) Int. Cl.
*A61F 2/42* (2006.01)
*A61B 17/56* (2006.01)
*A61B 17/80* (2006.01)

(52) U.S. Cl.
CPC ........ *A61B 17/562* (2013.01); *A61B 17/8061* (2013.01); *A61F 2/4202* (2013.01)

(58) Field of Classification Search
CPC .............................. A61B 17/562; A61F 2/4202
See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |
| 4,355,429 A | 10/1982 | Mittelmeier |
| 4,454,875 A | 6/1984 | Pratt |
| 4,484,570 A | 11/1984 | Sutter |
| 4,501,269 A | 2/1985 | Bagby |
| D281,814 S | 12/1985 | Pratt |
| 4,570,623 A | 2/1986 | Ellison |

(Continued)

FOREIGN PATENT DOCUMENTS

| | | |
|---|---|---|
| EP | 0179695 | 4/1986 |
| EP | 1327423 | 7/2003 |

(Continued)

*Primary Examiner* — Zade Coley
(74) *Attorney, Agent, or Firm* — Maywood IP Law; Stuart S. Bray; David Meibos (57) ABSTRACT

Systems for lower extremity fusion and arthroplasty include fusion spacers, bone plates, and articular prostheses fixed to bone by blade anchors. Examples are shown for anterior, lateral, and medial approaches.

17 Claims, 11 Drawing Sheets

(56) References Cited

U.S. PATENT DOCUMENTS

| | | |
|---|---|---|
| 4,611,581 A | 9/1986 | Steffee |
| 4,642,869 A | 2/1987 | Muller |
| 4,681,589 A | 7/1987 | Tronzo |
| 4,716,893 A | 1/1988 | Fischer |
| 4,743,256 A | 5/1988 | Brantigan |
| 4,743,262 A | 5/1988 | Tronzo |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,848,328 A | 7/1989 | Laboureau |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van Zile |
| 5,053,038 A | 10/1991 | Sheehan |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,352,229 A | 10/1994 | Goble |
| 5,366,479 A | 11/1994 | McGarry |
| 5,431,658 A | 7/1995 | Moskovich |
| 5,443,515 A | 8/1995 | Cohen |
| 5,449,359 A | 9/1995 | Groiso |
| 5,454,814 A | 10/1995 | Comte |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,660,188 A | 8/1997 | Groiso |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Brånemark |
| 5,772,661 A | 6/1998 | Michelson |
| 5,776,199 A | 7/1998 | Michelson |
| 5,776,202 A | 7/1998 | Copf |
| 5,788,701 A | 8/1998 | McCue |
| 5,800,550 A | 9/1998 | Sertich |
| 5,853,414 A | 12/1998 | Groiso |
| 5,860,973 A | 1/1999 | Michelson |
| 5,885,287 A * | 3/1999 | Bagby ............... A61F 2/44 623/16.11 |
| 5,893,889 A | 4/1999 | Harrington |
| 5,893,890 A | 4/1999 | Pisharodi |
| 5,947,999 A | 9/1999 | Groiso |
| 5,993,476 A | 11/1999 | Groiso |
| 6,039,762 A | 3/2000 | McKay |
| 6,063,121 A | 5/2000 | Xavier |
| 6,080,155 A | 6/2000 | Michelson |
| 6,096,080 A | 8/2000 | Nicholson |
| 6,102,949 A | 8/2000 | Biedermann |
| 6,113,638 A | 9/2000 | Williams |
| 6,120,503 A | 9/2000 | Michelson |
| 6,136,001 A | 10/2000 | Michelson |
| 6,159,214 A | 12/2000 | Michelson |
| 6,224,607 B1 | 5/2001 | Michelson |
| 6,235,059 B1 | 5/2001 | Benezech |
| 6,241,769 B1 | 6/2001 | Nicholson |
| 6,241,770 B1 | 6/2001 | Michelson |
| 6,270,498 B1 | 8/2001 | Michelson |
| 6,302,914 B1 | 10/2001 | Michelson |
| 6,309,421 B1 | 10/2001 | Pisharodi |
| 6,325,805 B1 | 12/2001 | Ogilvie |
| 6,336,928 B1 | 1/2002 | Guerin |
| 6,364,880 B1 | 4/2002 | Michelson |
| 6,402,785 B1 | 6/2002 | Zdeblick |
| 6,413,278 B1 | 7/2002 | Marchosky |
| 6,432,107 B1 | 8/2002 | Ferree |
| 6,436,098 B1 | 8/2002 | Michelson |
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,356 B2 | 7/2004 | Kanner |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |
| 6,923,810 B1 | 8/2005 | Michelson |
| 6,923,830 B2 | 8/2005 | Michelson |
| 6,926,718 B1 | 8/2005 | Michelson |
| 6,942,698 B1 * | 9/2005 | Jackson ............... A61F 2/4455 606/247 |
| 6,969,390 B2 | 11/2005 | Michelson |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 * | 6/2006 | Fraser ............... A61B 17/025 623/17.11 |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 * | 12/2008 | Fraser ............... A61B 17/025 623/17.11 |

(56) References Cited

U.S. PATENT DOCUMENTS

| | | | | |
|---|---|---|---|---|
| 7,481,830 | B2 | 1/2009 | Wall | |
| 7,481,832 | B1 | 1/2009 | Meridew | |
| D586,915 | S | 2/2009 | Grim | |
| 7,491,205 | B1 | 2/2009 | Michelson | |
| 7,503,933 | B2 | 3/2009 | Michelson | |
| 7,503,934 | B2 | 3/2009 | Eisermann | |
| 7,503,935 | B2 | 3/2009 | Zucherman | |
| D594,986 | S | 6/2009 | Miles | |
| 7,540,882 | B2 | 6/2009 | Michelson | |
| 7,556,650 | B2 | 7/2009 | Collins | |
| 7,572,293 | B2 | 8/2009 | Rhodes | |
| 7,588,600 | B2 | 9/2009 | Benzel | |
| 7,594,931 | B2 | 9/2009 | Louis | |
| 7,611,538 | B2 | 11/2009 | Belliard | |
| 7,658,766 | B2 | 2/2010 | Melkent | |
| 7,695,516 | B2 | 4/2010 | Zeegers | |
| 7,749,271 | B2 | 7/2010 | Fischer | |
| 7,763,076 | B2 | 7/2010 | Navarro | |
| 7,780,676 | B2 | 8/2010 | Lakin | |
| 7,837,732 | B2 | 11/2010 | Zucherman | |
| 7,850,791 | B2 | 12/2010 | Quadakkers | |
| 7,883,510 | B2 | 2/2011 | Kim | |
| 7,887,563 | B2 | 2/2011 | Cummins | |
| 7,896,919 | B2 | 3/2011 | Belliard | |
| 7,909,871 | B2 | 3/2011 | Abdou | |
| 7,918,891 | B1 | 4/2011 | Curran | |
| 7,966,799 | B2 | 6/2011 | Morgan | |
| 8,021,403 | B2 | 9/2011 | Wall | |
| 8,034,076 | B2 | 10/2011 | Criscuolo | |
| 8,100,972 | B1* | 1/2012 | Bruffey | A61F 2/442 623/17.11 |
| 8,100,974 | B2 | 1/2012 | Duggal | |
| 8,105,389 | B2 | 1/2012 | Berelsman | |
| 8,123,757 | B2 | 2/2012 | Zalenski | |
| 8,133,283 | B2 | 3/2012 | Wilson | |
| 8,157,865 | B2 | 4/2012 | Hochschuler | |
| 8,491,598 | B2 | 7/2013 | Crook | |
| 8,500,747 | B2 | 8/2013 | DeRidder | |
| 8,636,191 | B2 | 1/2014 | Meagher | |
| 8,747,412 | B2 | 6/2014 | Bae | |
| 8,808,294 | B2 | 8/2014 | Fox | |
| 9,254,130 | B2 | 2/2016 | Hollis | |
| 9,480,511 | B2 | 11/2016 | Butters | |
| 2001/0000532 | A1 | 4/2001 | Michelson | |
| 2001/0010001 | A1 | 7/2001 | Michelson | |
| 2001/0010002 | A1 | 7/2001 | Michelson | |
| 2001/0010020 | A1 | 7/2001 | Michelson | |
| 2001/0037154 | A1* | 11/2001 | Martin | A61F 2/3804 623/20.12 |
| 2001/0047207 | A1 | 11/2001 | Michelson | |
| 2001/0047208 | A1 | 11/2001 | Michelson | |
| 2002/0004683 | A1 | 1/2002 | Michelson | |
| 2002/0013624 | A1 | 1/2002 | Michelson | |
| 2002/0035400 | A1 | 3/2002 | Bryan | |
| 2002/0049447 | A1 | 4/2002 | Li | |
| 2002/0091390 | A1 | 7/2002 | Michelson | |
| 2002/0091392 | A1 | 7/2002 | Michelson | |
| 2002/0095155 | A1 | 7/2002 | Michelson | |
| 2002/0099376 | A1 | 7/2002 | Michelson | |
| 2002/0099378 | A1 | 7/2002 | Michelson | |
| 2002/0116065 | A1 | 8/2002 | Jackson | |
| 2002/0116165 | A1 | 8/2002 | El-Ghoroury | |
| 2002/0147454 | A1 | 10/2002 | Neto | |
| 2002/0147499 | A1 | 10/2002 | Shea | |
| 2002/0161443 | A1 | 10/2002 | Michelson | |
| 2002/0165613 | A1 | 11/2002 | Lin | |
| 2003/0023307 | A1 | 1/2003 | Michelson | |
| 2003/0040798 | A1 | 2/2003 | Michelson | |
| 2003/0045940 | A1 | 3/2003 | Eberlein | |
| 2003/0060884 | A1 | 3/2003 | Fell et al. | |
| 2003/0100949 | A1 | 5/2003 | Michelson | |
| 2003/0120344 | A1 | 6/2003 | Michelson | |
| 2003/0149483 | A1 | 8/2003 | Michelson | |
| 2003/0158553 | A1 | 8/2003 | Michelson | |
| 2003/0195517 | A1 | 10/2003 | Michelson | |
| 2003/0195561 | A1 | 10/2003 | Carley | |
| 2003/0195632 | A1 | 10/2003 | Foley | |
| 2004/0030336 | A1 | 2/2004 | Khanna | |
| 2004/0030339 | A1 | 2/2004 | Wack | |
| 2004/0034353 | A1 | 2/2004 | Michelson | |
| 2004/0064185 | A1 | 4/2004 | Michelson | |
| 2004/0073315 | A1 | 4/2004 | Justin | |
| 2004/0083005 | A1 | 4/2004 | Jacobsson | |
| 2004/0117018 | A1 | 6/2004 | Michelson | |
| 2004/0122518 | A1* | 6/2004 | Rhoda | A61F 2/44 623/17.11 |
| 2004/0133203 | A1 | 7/2004 | Young | |
| 2004/0148028 | A1 | 7/2004 | Ferree | |
| 2004/0176853 | A1 | 9/2004 | Sennett | |
| 2004/0193271 | A1 | 9/2004 | Fraser | |
| 2004/0199254 | A1 | 10/2004 | Louis | |
| 2004/0210313 | A1 | 10/2004 | Michelson | |
| 2004/0210314 | A1 | 10/2004 | Michelson | |
| 2004/0215203 | A1 | 10/2004 | Michelson | |
| 2004/0220668 | A1 | 11/2004 | Eisermann | |
| 2004/0220670 | A1 | 11/2004 | Eisermann | |
| 2004/0225295 | A1 | 11/2004 | Zubok | |
| 2004/0225365 | A1 | 11/2004 | Eisermann | |
| 2004/0230308 | A1 | 11/2004 | Michelson | |
| 2004/0249388 | A1 | 12/2004 | Michelson | |
| 2004/0254581 | A1 | 12/2004 | Leclair | |
| 2004/0254644 | A1 | 12/2004 | Taylor | |
| 2004/0260286 | A1* | 12/2004 | Ferree | A61F 2/28 623/17.11 |
| 2005/0004672 | A1 | 1/2005 | Pafford | |
| 2005/0014919 | A1 | 1/2005 | Hatakeyama | |
| 2005/0027300 | A1 | 2/2005 | Hawkins | |
| 2005/0038512 | A1 | 2/2005 | Michelson | |
| 2005/0038513 | A1 | 2/2005 | Michelson | |
| 2005/0043802 | A1 | 2/2005 | Eisermann | |
| 2005/0049600 | A1 | 3/2005 | Groiso | |
| 2005/0055031 | A1 | 3/2005 | Lim | |
| 2005/0125065 | A1 | 6/2005 | Zucherman | |
| 2005/0131545 | A1 | 6/2005 | Chervitz | |
| 2005/0143747 | A1 | 6/2005 | Zubok | |
| 2005/0149192 | A1 | 7/2005 | Zucherman | |
| 2005/0149193 | A1* | 7/2005 | Zucherman | A61B 17/1671 623/17.11 |
| 2005/0165408 | A1 | 7/2005 | Puno | |
| 2005/0171606 | A1 | 8/2005 | Michelson | |
| 2005/0171607 | A1 | 8/2005 | Michelson | |
| 2005/0177239 | A1 | 8/2005 | Steinberg | |
| 2005/0187628 | A1 | 8/2005 | Michelson | |
| 2005/0187629 | A1 | 8/2005 | Michelson | |
| 2005/0192586 | A1 | 9/2005 | Zucherman | |
| 2005/0216083 | A1 | 9/2005 | Michelson | |
| 2005/0216089 | A1 | 9/2005 | Michelson | |
| 2005/0234555 | A1 | 10/2005 | Sutton | |
| 2005/0273108 | A1 | 12/2005 | Groiso | |
| 2005/0277933 | A1 | 12/2005 | Wall | |
| 2006/0004453 | A1 | 1/2006 | Bartish | |
| 2006/0058802 | A1 | 3/2006 | Kofoed | |
| 2006/0074421 | A1 | 4/2006 | Bickley | |
| 2006/0079961 | A1 | 4/2006 | Michelson | |
| 2006/0085071 | A1 | 4/2006 | Lechmann | |
| 2006/0095136 | A1 | 5/2006 | McLuen | |
| 2006/0111787 | A1 | 5/2006 | Bailie | |
| 2006/0116769 | A1 | 6/2006 | Marnay | |
| 2006/0122702 | A1 | 6/2006 | Michelson | |
| 2006/0129238 | A1 | 6/2006 | Paltzer | |
| 2006/0136061 | A1 | 6/2006 | Navarro | |
| 2006/0136063 | A1* | 6/2006 | Zeegers | A61B 17/0642 623/17.14 |
| 2006/0142860 | A1 | 6/2006 | Navarro | |
| 2006/0149377 | A1 | 7/2006 | Navarro | |
| 2006/0149384 | A1 | 7/2006 | Navarro | |
| 2006/0167461 | A1 | 7/2006 | Hawkins | |
| 2006/0178745 | A1 | 8/2006 | Bartish | |
| 2006/0195097 | A1 | 8/2006 | Evans | |
| 2006/0212123 | A1* | 9/2006 | Lechmann | A61F 2/4425 623/17.15 |
| 2006/0241641 | A1 | 10/2006 | Albans | |
| 2006/0259143 | A1 | 11/2006 | Navarro | |
| 2006/0259145 | A1 | 11/2006 | Navarro | |

(56) References Cited

U.S. PATENT DOCUMENTS

| | | |
|---|---|---|
| 2006/0259146 A1 | 11/2006 | Navarro |
| 2007/0010890 A1 | 1/2007 | Collazo |
| 2007/0050032 A1 | 3/2007 | Gittings |
| 2007/0055376 A1 | 3/2007 | Michelson |
| 2007/0073404 A1 | 3/2007 | Rashbaum |
| 2007/0093839 A1 | 4/2007 | Beckendorf |
| 2007/0106388 A1 | 5/2007 | Michelson |
| 2007/0118132 A1 | 5/2007 | Culbert |
| 2007/0118145 A1 | 5/2007 | Fischer |
| 2007/0123903 A1 | 5/2007 | Raymond |
| 2007/0142922 A1 | 6/2007 | Lewis |
| 2007/0185375 A1 | 8/2007 | Stad |
| 2007/0191850 A1 | 8/2007 | Kim |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0015702 A1 | 1/2008 | Lakin |
| 2008/0051901 A1 | 2/2008 | de Villiers |
| 2008/0051902 A1 | 2/2008 | Dwyer |
| 2008/0103598 A1 | 5/2008 | Trudeau |
| 2008/0108997 A1 | 5/2008 | Berrevoets |
| 2008/0132949 A1 | 6/2008 | Aferzon |
| 2008/0140208 A1* | 6/2008 | Zucherman ............ A61F 2/4425 623/17.16 |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0069958 A1 | 3/2010 | Sullivan |
| 2010/0185287 A1 | 7/2010 | Allard |
| 2010/0185292 A1 | 7/2010 | Hochschuler |
| 2010/0201739 A1 | 8/2010 | Yamaguchi |
| 2010/0204737 A1* | 8/2010 | Bae ............ A61F 2/442 606/279 |
| 2010/0204739 A1* | 8/2010 | Bae ............ A61F 2/442 606/300 |
| 2011/0022176 A1 | 1/2011 | Zucherman |
| 2011/0098819 A1 | 4/2011 | Eisermann |
| 2011/0160766 A1 | 6/2011 | Hendren |
| 2011/0160866 A1* | 6/2011 | Laurence ........ A61B 17/1671 623/17.16 |
| 2011/0166608 A1 | 7/2011 | Duggal |
| 2012/0191204 A1* | 7/2012 | Bae .............. A61F 2/3859 623/20.31 |
| 2012/0215315 A1 | 8/2012 | Hochschuler |
| 2012/0239098 A1 | 9/2012 | Bae |
| 2012/0253406 A1* | 10/2012 | Bae .............. A61B 17/1671 606/279 |
| 2012/0265259 A1 | 10/2012 | LaPosta |
| 2012/0283837 A1* | 11/2012 | Bae .............. A61F 2/4455 623/17.16 |
| 2013/0013006 A1 | 1/2013 | Rashbaum |
| 2013/0123863 A1 | 5/2013 | Hollis |
| 2013/0190827 A1 | 7/2013 | Butters |
| 2013/0267956 A1 | 10/2013 | Terrill |
| 2014/0039632 A1 | 2/2014 | Hollis |
| 2016/0157906 A1 | 6/2016 | Hollis |

FOREIGN PATENT DOCUMENTS

| | | |
|---|---|---|
| EP | 1790298 | 5/2007 |
| EP | 1827318 | 9/2007 |
| EP | 1872746 | 1/2008 |
| EP | 1897517 | 3/2008 |
| EP | 1983941 | 10/2008 |
| EP | 2651341 | 10/2013 |
| EP | 2685938 | 8/2015 |
| EP | 3178448 | 6/2017 |
| WO | WO1993022990 | 11/1993 |
| WO | WO2000025707 | 5/2000 |
| WO | WO2000064360 | 11/2000 |
| WO | WO2001003570 | 1/2001 |
| WO | WO2002003885 | 1/2002 |
| WO | WO2002003895 | 1/2002 |
| WO | WO2002058593 | 8/2002 |
| WO | WO2003005939 | 1/2003 |
| WO | WO2003039400 | 5/2003 |
| WO | WO2003053290 | 7/2003 |
| WO | WO2003065930 | 8/2003 |
| WO | WO2003092507 | 11/2003 |
| WO | WO2004071359 | 8/2004 |
| WO | WO2004080355 | 9/2004 |
| WO | WO2004089240 | 10/2004 |
| WO | WO2004108015 | 12/2004 |
| WO | WO2005051243 | 6/2005 |
| WO | WO2005074841 | 8/2005 |
| WO | WO2006051547 | 5/2006 |
| WO | WO2006074414 | 7/2006 |
| WO | WO2006086494 | 8/2006 |
| WO | WO2006120505 | 11/2006 |
| WO | WO2006122194 | 11/2006 |
| WO | WO2007028098 | 3/2007 |
| WO | WO2007034310 | 3/2007 |
| WO | WO2007087366 | 8/2007 |
| WO | WO2008014258 | 1/2008 |
| WO | WO2008014453 | 1/2008 |
| WO | WO2008021955 | 2/2008 |
| WO | WO2008034140 | 3/2008 |
| WO | WO2008128367 | 10/2008 |
| WO | WO2009070721 | 6/2009 |
| WO | WO2010039026 | 4/2010 |
| WO | WO2010121002 | 10/2010 |
| WO | WO2011044879 | 4/2011 |
| WO | WO2011090508 | 7/2011 |
| WO | WO2012083205 | 6/2012 |
| WO | WO2012112598 | 8/2012 |

\* cited by examiner

BLADE FIXATION FOR ANKLE FUSION AND ARTHROPLASTY

CROSS-REFERENCE TO RELATED APPLICATIONS

This application is a continuation of:

U.S. patent application Ser. No. 13/747,791, filed Jan. 23, 2013, entitled BLADE FIXATION FOR ANKLE FUSION AND ARTHROPASTY, which is pending.

U.S. patent application Ser. No. 13/747,791 claims the benefit of:

U.S. Provisional Patent Application No. 61/589,721, filed Jan. 23, 2012, entitled BLADE FIXATION FOR ANKLE FUSION AND ARTHROPASTY.

The above-referenced documents are hereby incorporated by reference in their entirety.

This application incorporates by reference the following document in its entirety:

U.S. patent application Ser. No. 12/640,892, filed Dec. 17, 2009, entitled INTERVERTEBRAL IMPLANT WITH INTEGRATED FIXATION, which issued as U.S. Pat. No. 8,821,555 on Sep. 2, 2014.

BACKGROUND

Ankle fusion rates are negatively affected, and ankle arthroplasty revision rates increase, due to the loads, stresses, high range of motion, and complex motion of the ankle joint. Secure fixation of the ankle during fusion and secure fixation of the ankle arthroplasty components contribute to the success of the procedure by preventing post-operative loosening or subsidence of components. Leg-length discrepancies are also common pre- and post-operatively, thus there is a need to restore leg length with a fusion or arthroplasty implant. There is also a need for easy, repeatable, secure ankle fixation devices and methods.

SUMMARY

@In an aspect of the technology, a system includes a first implant body with a first bone-contacting surface and a first channel on the first bone-contacting surface; and a first anchor coupled to the first implant body, the first anchor including a first bone fixation feature carried outside the first implant body, a first connecting feature fixed in the first channel, and a first intermediate portion connecting the first bone fixation feature to the first connecting feature, wherein the first intermediate portion extends through the first bone-contacting surface; wherein the first channel and the first connecting feature have complementary interconnecting shapes, wherein the first connecting feature slidingly engages the first channel to couple the first anchor to the first implant body.

In an embodiment, the system includes a second anchor like the first anchor; wherein the second anchor is coupled to the first implant body.

In another embodiment, the second anchor is coupled to the first channel.

In yet another embodiment, the second anchor is coupled to a second channel on a second bone-contacting surface of the body.

In yet another embodiment, the second anchor is coupled to a second channel on the first bone-contacting surface.

In yet another embodiment, the system includes a third anchor like the first anchor; wherein the third anchor is coupled to the first implant body.

In yet another embodiment, the third anchor is coupled to a third channel on a second bone-contacting surface of the body.

In yet another embodiment, the system includes a fourth anchor like the first anchor; wherein the fourth anchor is coupled to the first implant body.

In yet another embodiment, the fourth anchor is coupled to a fourth channel on the second bone-contacting surface of the body.

BRIEF DESCRIPTION OF THE DRAWINGS

While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the technology described herein can be included within the scope of the present technology.

In the following Detailed Description, various features are grouped together in several embodiments for the purpose of streamlining the disclosure. This method of disclosure is not to be interpreted as reflecting an intention that exemplary embodiments of the technology require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear. Similar reference numbers (e.g., those that are identical except for the first numeral) are used to indicate similar features in different embodiments.

DETAILED DESCRIPTION

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

The present technology may be employed in a fusion spacer with integrated blade anchor fixation. The spacer includes a body disposed between at least two bones or bone portions. The body includes channels to accept one or more fixation blades, or anchors, per bone/implant interface. In other words, the body includes at least one channel on each bone-contacting surface, and may include more than one channel per bone-contacting surface. Each channel may accept one or more fixation blade anchors. The body may also include at least one hole or fenestration that extends between bone-contacting surfaces. The hole may be centrally located. The hole may contain bone fusion material, such as autograft bone, allograft bone, demineralized bone matrix (DBM), osteoconductive, or osteoinductive agents, among others. Each fixation blade, or anchor, may slide into a corresponding channel, and at the same time, into an adjacent portion of bone. The fixation blade, or anchor, may be impacted into the channel and bone portion. The fixation blade anchor may lock to the fusion spacer upon insertion so that the anchor may not migrate or be unintentionally removed from the fusion spacer. The anchor and/or fusion spacer may include integrated locking features or mechanisms so that locking occurs automatically as the anchor reaches full insertion. As the fixation blade, or anchor, advances into the channel and bone portion, the body and bone portion may be urged into compression. Additional fixation devices may also be included, such as pegs, stems, keels, screws, and the like.

Figure 1:
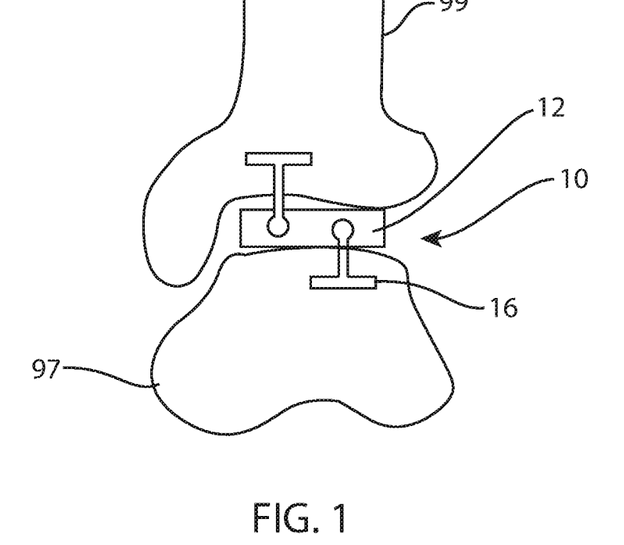
FIG. 1 is a front view of a left tibiotalar joint with a fusion spacer secured within the joint.
Figure 2:
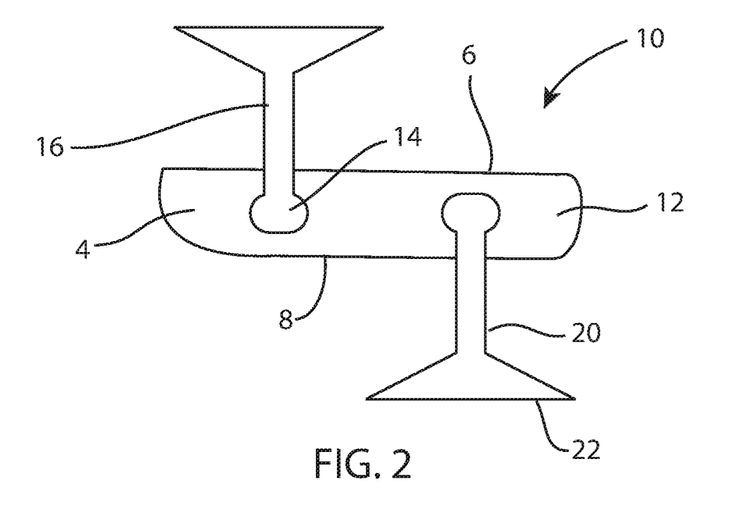
FIG. 2 is a front view of the fusion spacer of FIG. 1.

FIGS. 1-2, 4, and 11 illustrate an example of a fusion spacer for an anterior approach to an ankle joint. Fusion spacer 10 includes a body 12 that may be disposed between a tibia 99 and a talus 97 as shown in FIG. 1 in an anterior view of an ankle joint. This example may be implanted through an anterior approach, although other examples may be implanted through other approaches. The body 12 includes two bone-contacting surfaces 6, 8 and a perimeter surface 4 extending around the body between the bone-contacting surfaces. Surface 6 is a tibia-contacting surface and surface 8 is a talus-contacting surface. Surface 6 may be straight across in an anterior view (FIGS. 1-2) and may be convex in a lateral view (FIGS. 4 and 11) in order to approximate a distal articular surface of a tibia. Surface 8 may be straight across in an anterior view (FIGS. 1-2) and may be concave in a lateral view (FIGS. 4 and 11) in order to approximate a proximal articular surface of a talus. Surfaces 6, 8 may be sections of cylinders, or semi-cylindrical. In other examples, the bone-contacting surfaces may be shaped differently to suit the particular implantation site. The body 12 may also include at least one hole 11 or fenestration that extends between bone-contacting surfaces. The hole 11 may be centrally located or off-center. The hole 11 may contain bone fusion material, such as autograft bone, allograft bone, demineralized bone matrix (DBM), osteoconductive, or osteoinductive agents, among others. The body may include at least one channel 14 on each bone-contacting surface 6, 8. The body 12 may include a plurality of channels 14 that accept at least one fixation blade anchor 16 for each bone-implant interface. Each channel 14 may include an undercut keyway which is complementary to a portion of the blade anchor 16. The channels 14 in this example are oriented to extend in an anterior-posterior direction when the fusion spacer 10 is implanted.

The blade anchors 16 may include a connecting feature 18, such as a knob, hook, key, tee, dovetail, rail, or other feature designed for complementary interconnecting fit with the channel 14 on the spacer body 12. The blade anchors 16 may be substantially T-shaped, and include an elongated intermediate portion 20 and a bone fixation feature 22.

The anchors in the present disclosure may share some or all of the features of the anchors disclosed in U.S. patent application Ser. No. 12/640,892 to Bae, et al., which is incorporated by reference herein in its entirety.

In use, the distal tibia and proximal talus may be exposed from an anterior approach, and the bones prepared with cutting instruments, jigs, and other tools to remove damaged, diseased, or otherwise undesirable articular cartilage and/or bone. This bone preparation establishes resection surfaces on the tibia and talus, which may be geometric approximations or idealizations of the removed natural bone surfaces, or undamaged natural bone surfaces. The resection surfaces may also match or complement the corresponding bone-facing surfaces on the spacer body 12. In this example, a distal tibial resection surface (not shown) may be straight across in an anterior view and convex in a lateral view. A proximal talar resection surface (not shown) may be straight across in an anterior view and concave in a lateral view. Trial bodies may be inserted into the tibiotalar joint space from an anterior direction to determine an appropriate length, width, thickness, height, and/or varus/valgus tilt for the spacer body 12. The appropriately sized spacer body 12 may then be selected from a kit or set of spacer bodies and inserted into the joint space from an anterior direction. The anchors 16 may then be aligned with the corresponding channels 14 and slidingly inserted into the channels and adjacent bone portions from an anterior direction. Additional tools may be used in this step to facilitate anchor alignment and insertion.

Figure 4:
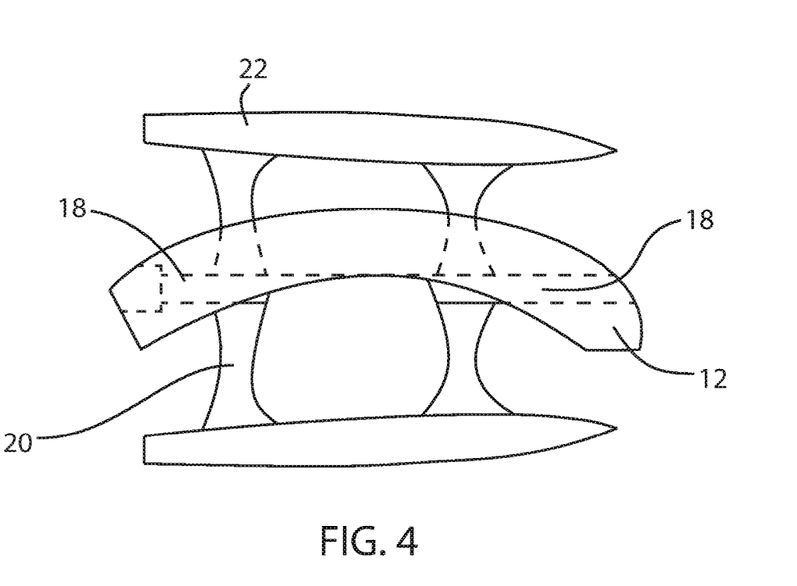
FIG. 4 is a side view of the fusion spacer of FIG. 1.

Referring to FIG. 4, the connecting feature 18, or rail, may be interrupted or intermittent along the length of the blade anchor 16, or the rail may be continuous.

Figure 6:
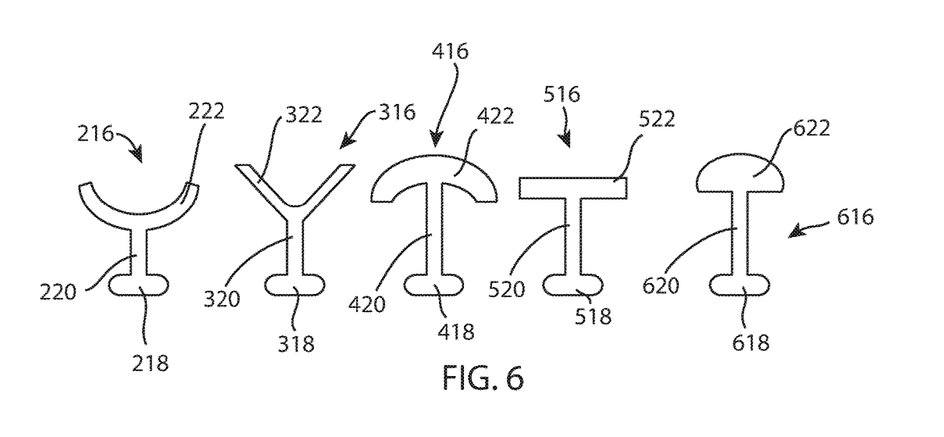
FIG. 6 is a front view of a set of anchors, each having a different cross sectional shape.

FIG. 6 illustrates some alternative configurations for the bone-anchoring blades 16, as viewed from an end, or in other words, along an insertion direction. Each of the alternative anchor configurations 216, 316, etc. is distinguished by a bone fixation feature 222, 322, etc. and a connection feature 218, 318, etc. coupled together by an intermediate portion 220, 320, etc. The intermediate portion is narrower than either the bone fixation feature or the connection feature. In other words, the bone fixation feature and the connection feature are each wider than the intermediate portion. This arrangement, in the illustrated examples and others like them, enables the anchor 16 (specifically the intermediate portion) to perform as a tension-compression member to transfer tensile and compressive loads between the body and the adjacent bone portion.

Figure 3:
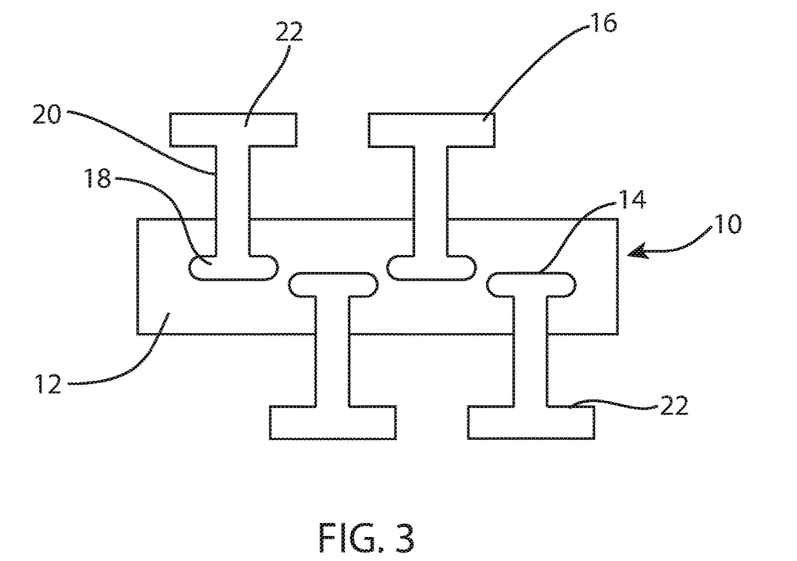
FIG. 3 is a front view of another fusion spacer.

FIG. 3 illustrates another example of a fusion spacer 110 for anterior insertion. Spacer 110 includes a body 112 with two channels 114 on each bone-contacting surface 106, 108. In this example, the channels 114 alternate between surface 6 and surface 8 across a width of the body 112. Other characteristics of spacer 110 may be similar to, or identical to, those of spacer 10, including the orientation of the channels 114.

Figure 12:
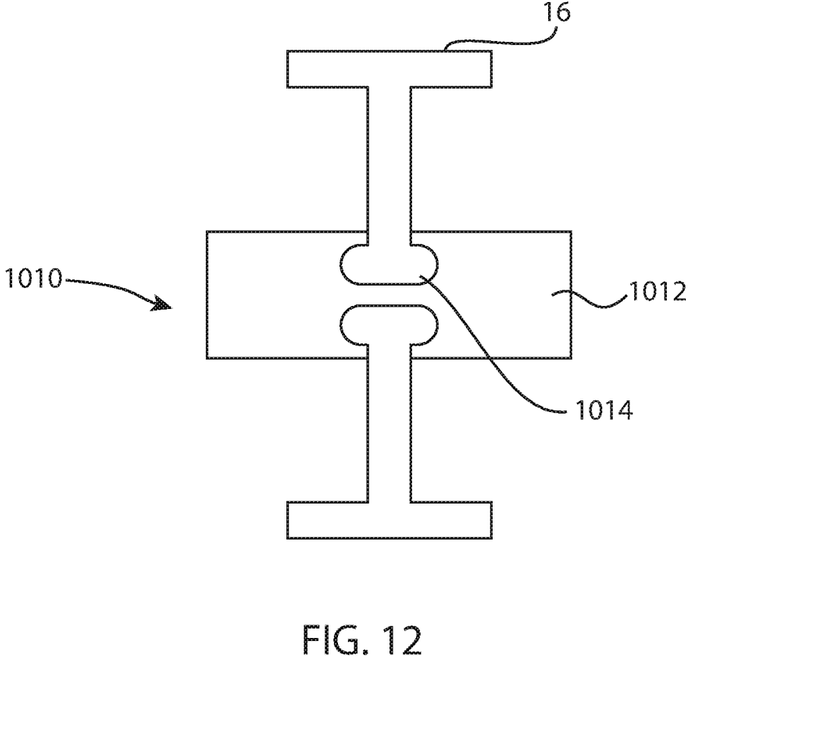
FIG. 12 is a front view of yet another fusion spacer.
Figure 13:
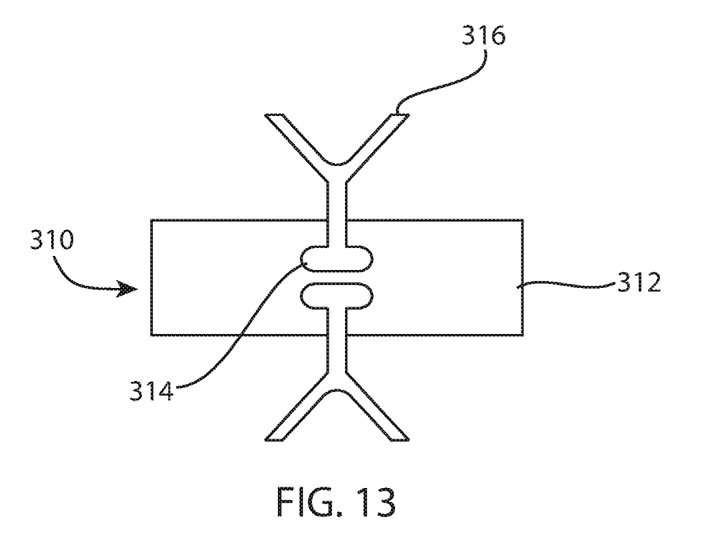
FIG. 13 is a front view of yet another fusion spacer.
Figure 14:
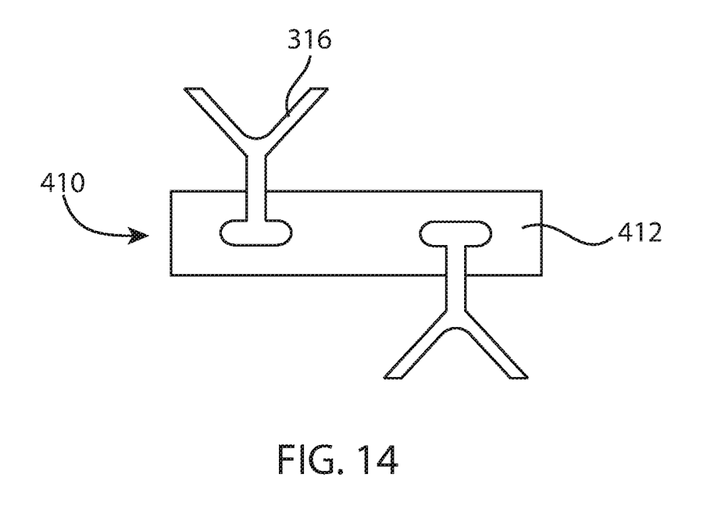
FIG. 14 is a front view of yet another fusion spacer.

FIGS. 12-14 show yet more examples of fusion spacers for anterior approach to the ankle joint. FIG. 12 shows a fusion spacer 1010 with a body 1012 having channels 1014 directly opposite each other. FIG. 13 also shows a fusion spacer 310 with a body 312 having channels 314 directly opposite each other. This example includes anchor 316. FIG. 14 shows a spacer 410 with a body 412 and anchor 316. Body 412 may be identical to body 12.

Figure 5:
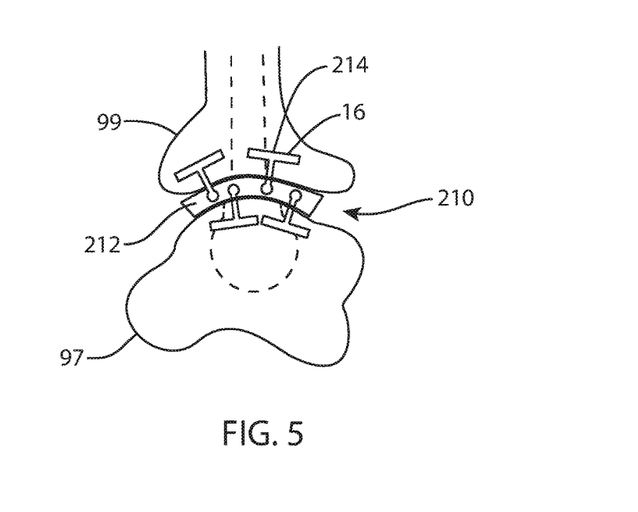
FIG. 5 is a side view of a left tibiotalar joint with yet another fusion spacer secured within the joint.
Figure 18:
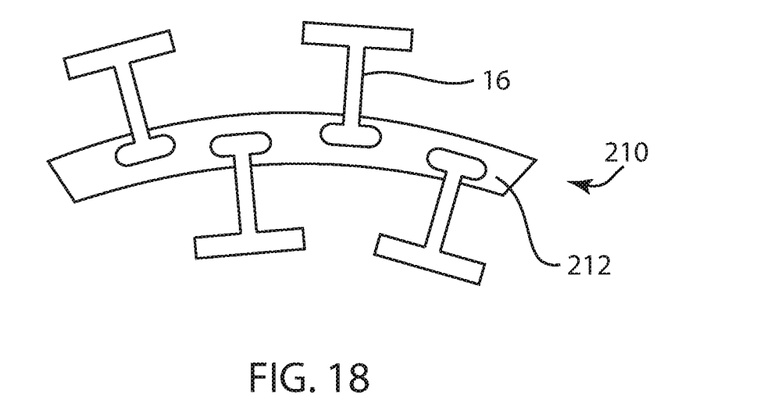
FIG. 18 is a side view of the fusion spacer of FIG. 5.
Figure 21:
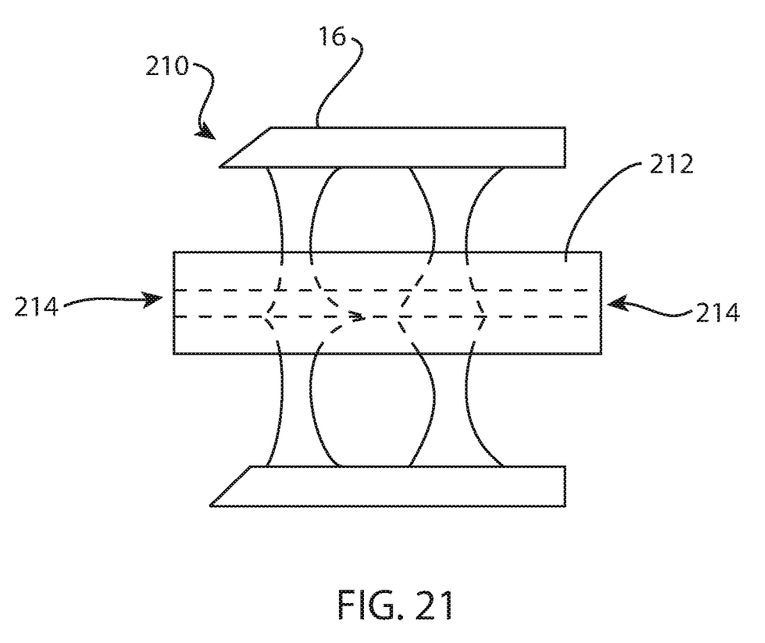
FIG. 21 is a front view of the fusion spacer of FIG. 5.

FIGS. 5, 18, and 21 illustrate yet another example of a fusion spacer 210, this time for lateral or medial insertion. The spacer body 212 may resemble spacer 12, at least with regards to the bone-contacting surfaces 6, 8; the perimeter surface 4; and optionally the fenestration 11. However, in this example, channels 214 extend in a medial-lateral direction when the fusion spacer 210 is implanted. Like spacer 110, spacer 210 includes two channels on each bone-contacting surface, the channels alternating between the bone-contacting surfaces across a width of the body 212.

Figure 15:
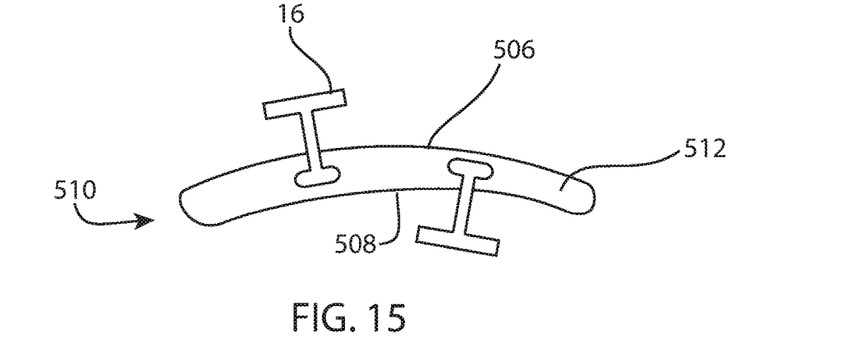
FIG. 15 is a side view of yet another fusion spacer.
Figure 16:
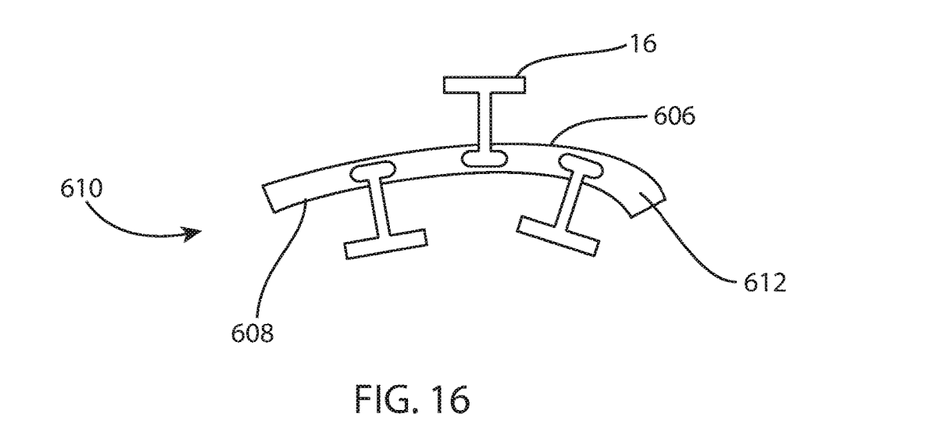
FIG. 16 is a side view of yet another fusion spacer.
Figure 17:
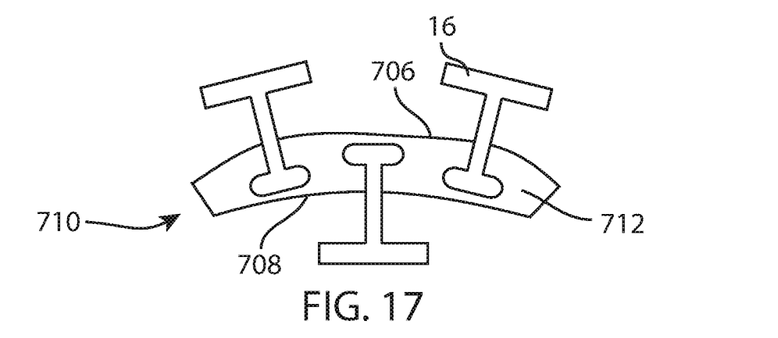
FIG. 17 is a side view of yet another fusion spacer.
Figure 19:
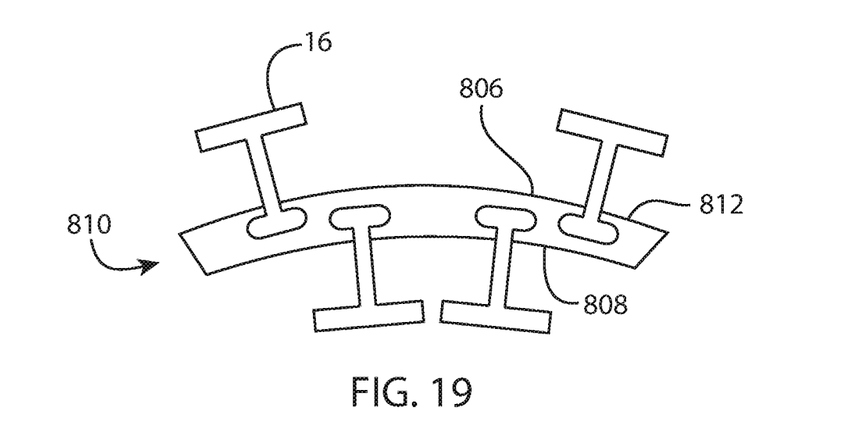
FIG. 19 is a side view of yet another fusion spacer.
Figure 20:
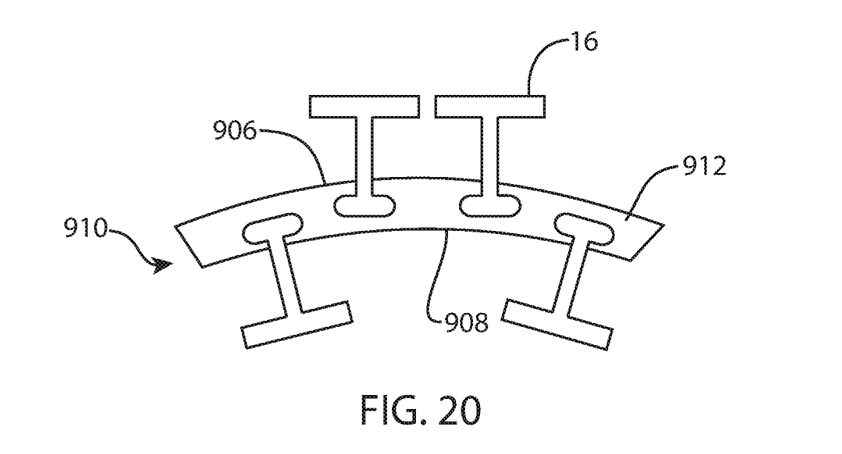
FIG. 20 is a side view of yet another fusion spacer.

FIGS. 15-17 and 19-20 show yet more examples of fusion spacers for lateral or medial approach to the ankle joint. FIG. 15 shows a fusion spacer 510 with a body 512 carrying one anchor 16 on each bone-contacting surface 506, 508. FIG. 16 shows a fusion spacer 610 with a body 612 carrying one anchor 16 centrally located on bone-contacting surface 606 and two anchors 16 bilaterally offset from center of bone-contacting surface 608. FIG. 17 shows a fusion spacer 710 with an opposite configuration, in which body 712 carries one anchor 16 centrally located on bone-contacting surface 708 and two anchors 16 bilaterally offset from center of bone-contacting surface 706. FIG. 19 shows a fusion spacer 810 with a body 812 carrying two anchors 16 widely bilaterally offset from center of bone-contacting surface 806 and two anchors 16 narrowly bilaterally offset from center of bone-contacting surface 808. FIG. 20 shows a fusion spacer 910 with an opposite configuration, in which body 912 carries carrying two anchors 16 widely bilaterally offset from center of bone-contacting surface 908 and two anchors narrowly bilaterally offset from center of bone-contacting surface 906. Other arrangements are contemplated, both symmetric and asymmetric.

The fusion spacers disclosed herein may be adapted for use in midfoot and/or forefoot fusion procedures, such as tarsometatarsal joint fusion, hallucal fracture fusion, and the like.

The present technology may be employed in a bone plate with integrated blade anchor fixation. The plate may extend across at least two bones or bone portions. For example, the plate may extend across two bones and a joint therebetween, or between two bone fragments and a fracture or intentional cut therebetween. The plate includes channels to accept one or more fixation blades, or anchors, per bone/implant interface. In other words, the plate includes at least one channel for each bone or bone fragment to be fixed to the plate, and may include more than one channel for each bone or bone fragment to be fixed to the plate. The bone plate may be said to have a separate bone-contacting surface, area, or region for each bone or bone fragment to be fixed to the plate. Each channel may accept one or more fixation blade anchors. Each fixation blade, or anchor, may slide into a corresponding channel, and at the same time, into an adjacent portion of bone. The fixation blade may be impacted into the channel and bone portion. The fixation blade anchor may lock to the bone plate upon insertion so that the anchor may not migrate or be unintentionally removed from the bone plate. The anchor and/or bone plate may include integrated locking features or mechanisms so that locking occurs automatically as the anchor reaches full insertion. As the fixation blade advances into the channel and bone portion, the plate and bone portion may be urged into compression. Additional fixation devices may also be included, such as pegs, stems, keels, screws, and the like.

Figure 7:
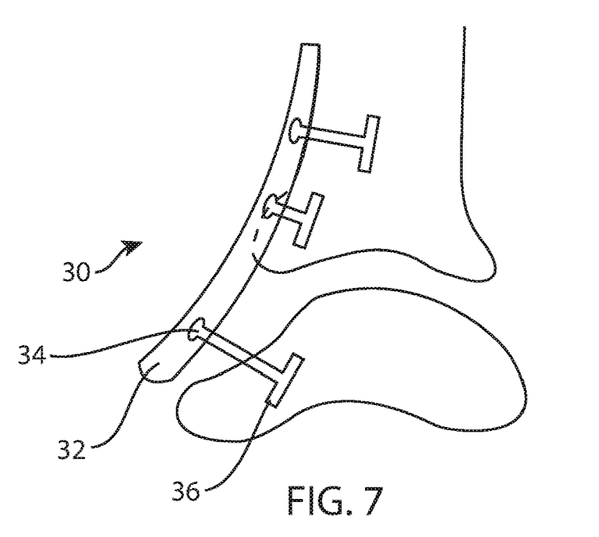
FIG. 7 is a side view of a left tibiotalar joint with a fusion plate secured across the joint.

FIG. 7 illustrates an example of a bone plate system 30 for anterior application across an ankle joint for fusion. Bone plate system 30 includes a plate body 32 that extends anteriorly across a distal portion of a tibia and a proximal portion of a talus with a plurality of channels 34 configured to receive one or more fixation blade anchors 36. The channels 34, blade anchors 36, and their configuration on the plate body 32 may be similar to those described above with regard to FIGS. 1-6 and 11-20. However, this example provides an opportunity to mention that any of the anchors disclosed herein may have different heights, or depth of penetration into an adjacent bone portion. Any of the blade anchor shapes or sizes disclosed herein may be used. The plate body 32 carries three anchors 34, the outermost anchors penetrating deeply into adjacent bone and the middle one penetrating relatively shallowly.

The fusion plate body 32 may also include at least one aperture to provide for bone fusion material. The aperture may be located anywhere along the plate body 32. For example, an aperture may be adjacent to a channel 34 or between two channels.

In use, the distal tibia and proximal talus may be exposed from an anterior approach. Optionally, the bones may be prepared with cutting instruments, jigs, and other tools to remove damaged, diseased, or otherwise undesirable periosteum, articular cartilage, and/or bone. This bone preparation establishes resection surfaces on the tibia and talus, which may be geometric approximations or idealizations of the removed natural bone surfaces, or undamaged natural bone surfaces. The resection surfaces may also match or complement the corresponding bone-facing surfaces on the plate body 32. In this example, however, extensive bone preparation is not shown. Trial plate bodies may be applied to the exposed tibiotalar region from an anterior direction to determine an appropriate length, width, thickness, height, and/or curvature for the plate body 32. Measuring instruments may be used instead of trials. The appropriately sized plate body 32 may then be selected from a kit or set of plate bodies and applied to the exposed tibiotalar region from an anterior direction. The anchors 36 may then be aligned with the corresponding channels 34 and inserted into the channels and adjacent bone portions from a lateral or medial direction. Additional tools may be used in this step to facilitate anchor alignment and insertion. In another example, the channels 34 may be oriented in an anterior-posterior direction and anchors 36 may be inserted along an anterior or posterior direction.

Figure 8:
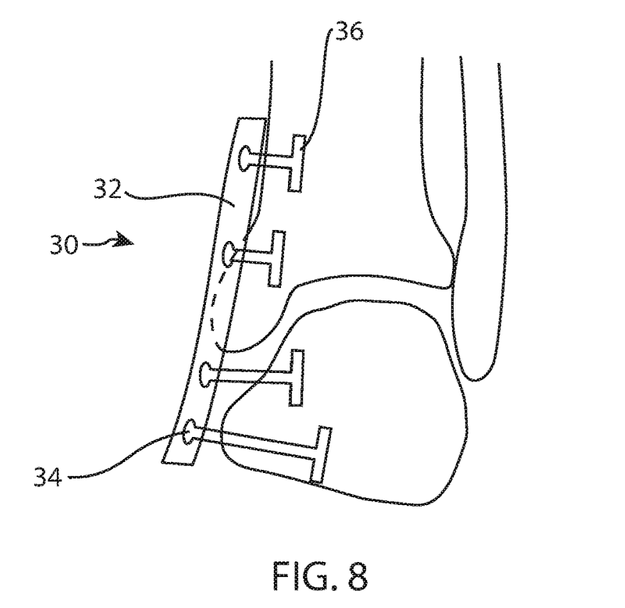
FIG. 8 is a front view of a left tibiotalar joint with another fusion plate secured across the joint.

FIG. 8 illustrates another example of a bone plate system 130, this time for lateral or medial application across an ankle joint for fusion. The plate body 132 may at least partially resemble plate body 32. However, in this example, channels 134 extend in an anterior-posterior direction when the bone plate system 130 is implanted. This example further illustrates the anchors 136 having different depths of penetration into adjacent bone, or otherwise different lengths of protrusion from the plate body 132. The distal most anchor in this example has the greatest penetration, the proximal most two anchors have the least penetration, and the second from distal most anchor has an intermediate depth of penetration. In another example, the channels 134 may be oriented in a medial-lateral direction and anchors 136 may be inserted along a lateral or medial direction. When applied laterally, the tibia, talus, and/or fibula each may receive at least one blade anchor.

The bone plates disclosed herein may be adapted for use in midfoot and/or forefoot fusion procedures, such as fracture fixation, opening and/or closing wedge osteotomy fixation, joint fusion, and the like.

The present technology may be employed in an arthroplasty device with integrated blade anchor fixation. The arthroplasty device, or prosthesis, may include first and second endplates, or bone-contacting components, and an articular core disposed between the bone-contacting components. Each bone-contacting component includes at least one channel on each bone-contacting surface to accept one or more fixation blades, or anchors. In other words, each bone-contacting component includes at least one channel per bone/implant interface. More than one channel may be included on each bone-contacting surface. Each channel may accept one or more fixation blade anchors. Each fixation blade, or anchor, may slide into a corresponding channel, and at the same time, into an adjacent portion of bone. The fixation blade may be impacted into the channel and bone portion. The fixation blade anchor may lock to the bone-contacting component upon insertion so that the anchor may not migrate or be unintentionally removed from the bone-contacting component. The anchor and/or bone-contacting component may include integrated locking features or mechanisms so that locking occurs automatically as the anchor reaches full insertion. As the fixation blade advances into the channel and bone portion, the bone-contacting component and bone portion may be urged into compression. Additional fixation devices may also be included, such as pegs, stems, keels, screws, and the like.

Figure 9:
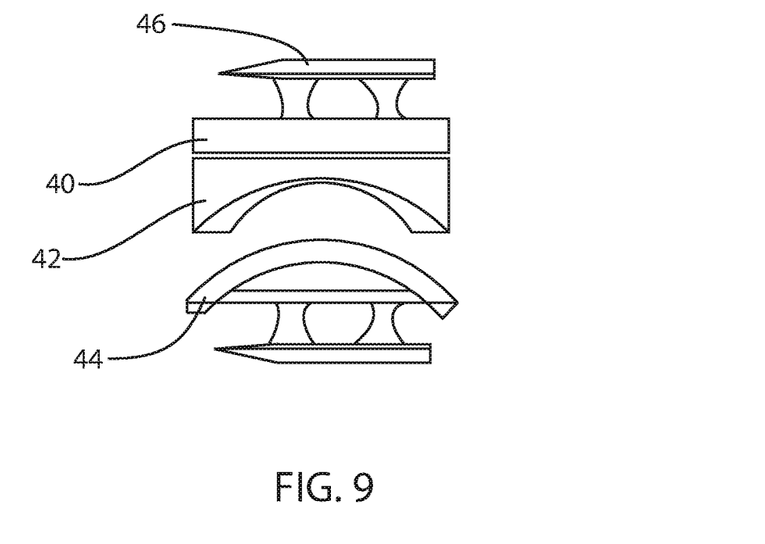
FIG. 9 is an exploded side view of an ankle arthroplasty device.
Figure 10:
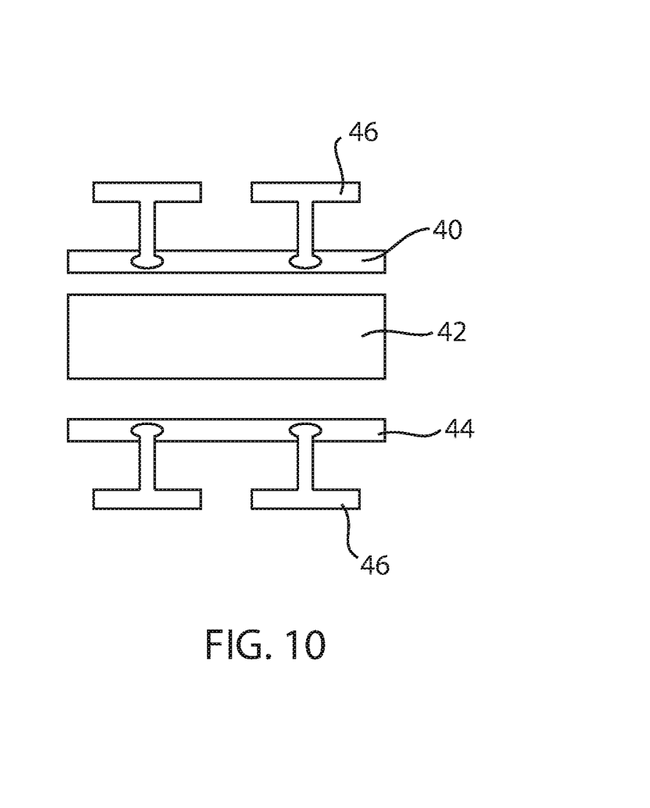
FIG. 10 is an exploded front view of the ankle arthroplasty device of FIG. 9.
Figure 11:
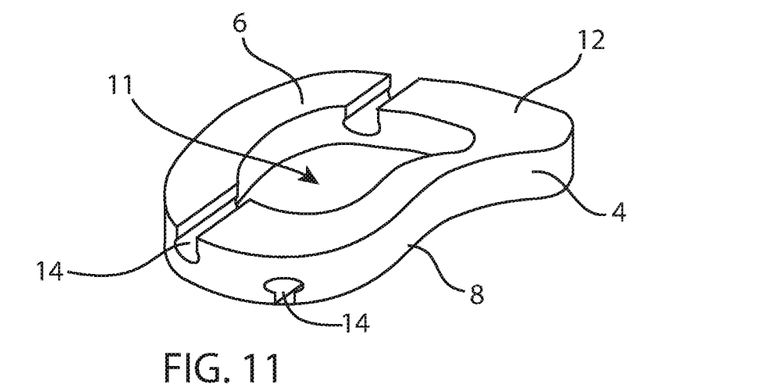
FIG. 11 is an isometric view of a body of the fusion spacer of FIG. 1.

As illustrated in FIGS. 9 and 10, an ankle arthroplasty prosthesis 41 includes a tibial endplate 40, an articulating core 42, and a talar endplate 44. Similar to the previously described examples, the tibial endplate 40 and the talar endplate 44 each may have at least one channel 45 in a bone-contacting surface. Each channel 45 may be configured to accept at least one fixation blade 46. Any of the blade anchor shapes or sizes disclosed herein may be used. The fixation blade anchors 46 may be inserted anteriorly, as shown in this example, or laterally or medially, by reorienting the channels as described above for the fusion spacers and/or bone plates. In practice, the fixation blades 46 may be impacted into the bone, resulting in compression between the endplate and the bone to achieve good compression to achieve good short-term and long-term fixation of the prosthesis. The surgical method may be similar to the method described above for fusion spacers.

The arthroplasty prostheses disclosed herein may be adapted for use in midfoot and/or forefoot arthroplasty procedures, such as hallux valgus, hammertoe, and the like.

The components disclosed herein may be made from metals, polymers, ceramics, glasses, composite materials, biological materials or tissues, or other biocompatible materials. Different materials may be used for individual components. Different materials may be combined in a single component.

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase (s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A system comprising:
   an implant body comprising a concave surface configured to contact bone and a channel extending across the concave surface between a leading portion of the channel and a trailing portion of the channel, wherein the channel comprises an undercut keyway, wherein the undercut keyway is discontinuous between the trailing portion of the channel and the leading portion of the channel; and
   an anchor comprising a fixation feature for engaging bone, a connecting feature extending along a length of the anchor, and an intermediate portion connecting the fixation feature to the connecting feature, wherein the connecting feature comprises a leading part and a trailing part, wherein the leading part of the connecting feature is discontinuous from the trailing part of the connection feature;

wherein the channel and the connecting feature have complementary interconnecting shapes, wherein the connecting feature slidingly engages the channel to couple the anchor to the implant body;

wherein, when the anchor is coupled to the implant body, the leading part of the connecting feature is fixed in the leading portion of the channel, the trailing part of the connecting feature is fixed in the trailing portion of the channel, at least a portion of the connecting feature between the leading and trailing portions of the channel is carried outside the concave surface, and the fixation feature is carried outside the implant body.

2. The system of claim 1, wherein the channel comprises a slot extending from the undercut keyway outwardly through the concave surface, wherein the undercut keyway comprises a first wall and a second wall opposite the first wall, wherein the slot extends through the first wall, wherein the concave surface intersects a portion of the first wall.

3. The system of claim 2, wherein the channel has a longitudinal axis, which is oblique to the concave surface at the second wall.

4. The system of claim 2, wherein the concave surface intersects a portion of the second wall.

5. The system of claim 1, wherein the implant body is an ankle fusion spacer.

6. The system of claim 1, wherein the implant body is an ankle arthroplasty component.

7. A system comprising:
an implant body comprising a concave surface configured to contact bone and a channel extending across the concave surface between a leading portion of the channel and a trailing portion of the channel, wherein the channel comprises an undercut keyway, wherein the undercut keyway is discontinuous and separates the trailing portion of the channel from the leading portion of the channel; and an anchor comprising a fixation feature for engaging bone, a connecting feature extending along a length of the anchor, and an intermediate portion connecting the fixation feature to the connecting feature, wherein the connecting feature comprises a leading part and a trailing part, wherein the leading part of the connecting feature is discontinuous from the trailing part of the connecting feature;

wherein the channel and the connecting feature have complementary interconnecting shapes, wherein the connecting feature slidingly engages the channel to couple the anchor to the implant body;

wherein, when the anchor is coupled to the implant body, the leading part of the connecting feature is fixed in the leading portion of the channel, the trailing part of the connecting feature is fixed in the trailing portion of the channel, at least a portion of the connecting feature between the leading and trailing portions of the channel is carried outside the concave surface, and the fixation feature is carried outside the implant body.

8. The system of claim 7, wherein the channel comprises a slot extending from the undercut keyway outwardly through the concave surface, wherein the undercut keyway comprises a first wall and a second wall opposite the first wall, wherein the slot extends through the first wall, wherein the concave surface intersects a portion of the first wall.

9. The system of claim 8, wherein the channel has a longitudinal axis, which is oblique to the concave surface at the second wall.

10. The system of claim 8, wherein the concave surface intersects a portion of the second wall.

11. The system of claim 7, wherein the implant body is an ankle fusion spacer.

12. The system of claim 7, wherein the implant body is an ankle arthroplasty component.

13. A system comprising:
an implant body comprising a concave surface configured to contact bone and a channel extending across the concave surface between a leading portion of the channel and a trailing portion of the channel, wherein the channel comprises an undercut keyway and a middle portion, wherein the middle portion of the channel is between the leading and trailing portions of the channel, so that the channel is discontinuous between the leading portion of the channel and the trailing portion of the channel; and an anchor comprising a fixation feature for engaging bone, a connecting feature extending along a length of the anchor, and an intermediate portion connecting the fixation feature to the connecting feature, wherein the connecting feature comprises a leading part and a trailing part, wherein the leading part of the connecting feature is discontinuous from the trailing part of the connecting feature;

wherein the channel and the connecting feature have complementary interconnecting shapes, wherein the connecting feature slidingly engages the channel to couple the anchor to the implant body;

wherein, when the anchor is coupled to the implant body, the leading part of the connecting feature is fixed in the leading portion of the channel, the trailing part of the connecting feature is fixed in the trailing portion of the channel, at least a portion of the connecting feature between the leading and trailing portions of the channel is carried outside the concave surface, and the fixation feature is carried outside the implant body.

14. The system of claim 13, wherein the channel comprises a slot extending from the undercut keyway outwardly through the concave surface, wherein the undercut keyway comprises a first wall and a second wall opposite the first wall, wherein the slot extends through the first wall, wherein the concave surface intersects a portion of the first wall.

15. The system of claim 14, wherein the channel has a longitudinal axis, which is oblique to the concave surface at the second wall.

16. The system of claim 14, wherein the concave surface intersects a portion of the second wall.

17. The system of claim 13, wherein the implant body is selected from the group consisting of an ankle fusion spacer and an ankle arthroplasty component.

* * * * *